United States Patent
Augelli-Szafran et al.

(10) Patent No.: US 6,500,837 B2
(45) Date of Patent: Dec. 31, 2002

(54) FUSED RING SYSTEM CONTAINING INDOLE AS $M_4$ SELECTIVE AZA-ANTHRACENE MUSCARINIC RECEPTOR ANTAGONISTS

(75) Inventors: Corinne Elizabeth Augelli-Szafran, Ann Arbor, MI (US); Thomas M. Boehme, Rüsselsheim (DE)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/952,735

(22) Filed: Sep. 14, 2001

(65) Prior Publication Data
US 2002/0068752 A1 Jun. 6, 2002

Related U.S. Application Data
(60) Provisional application No. 60/234,826, filed on Sep. 22, 2000.

(51) Int. Cl.⁷ .................. A61K 31/4745; C07D 471/04; A61P 25/16
(52) U.S. Cl. ..................... 514/280; 546/53; 546/50
(58) Field of Search .................... 546/53, 50; 514/280

(56) References Cited

PUBLICATIONS

European Search Report (SN 01122280.9).
Augelli–Szafran et al., "Identification and Characterization of m4 Selective Muscarinic Antagonists", *Bioorganic & Medicinal Chemistry Letters*, vol. 8, pp 1991–1996, 1998.

Primary Examiner—Evelyn Mei Huang

(74) Attorney, Agent, or Firm—David R. Kurlandsky; Charles W. Ashbrook

(57) ABSTRACT

Disclosed are compounds of the Formula I

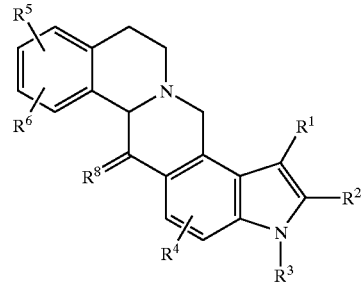

and pharmaceutically acceptable salts, esters, amides, and prodrugs thereof,
wherein
$R^1$ is hydrogen, lower alkyl, $COOR^7$, (un)substituted aryl, (un)substituted heteroaryl, (un)substituted arylalkyl, or (un)substituted heteroarylalkyl;
$R^3$ is hydrogen or lower alkyl;
$R^2$, $R^4$, $R^5$, and $R^6$ independently represent hydrogen, halogen, lower alkyl, lower alkoxy, hydroxy, cyano, nitro, amino, mono- or dialkylamino, carboxy, alkoxycarbonyl, carbamoyl, sulfamoyl, trifluoromethyl, or alkylthio;
$R^7$ is hydrogen or lower alkyl; and
$R^8$ is hydrogen or oxo.
Also provided is a method for selectively antagonizing the $M_4$ muscarinic receptor and a method for treating Parkinson's disease.

15 Claims, No Drawings

FUSED RING SYSTEM CONTAINING INDOLE AS M₄ SELECTIVE AZA-ANTHRACENE MUSCARINIC RECEPTOR ANTAGONISTS

This application claims the benefit of provisional application No. 60/234826, filed on Sep. 22, 2000.

FIELD OF THE INVENTION

This invention relates to fused-ring compounds containing an indole. This invention further relates to compounds that selectively bind to the $M_4$ muscarinic receptor. In addition, this invention relates to a method of treating Parkinson's disease.

BACKGROUND OF THE INVENTION

Parkinson's disease (PD) is a progressive neurodegenerative disease characterized by hypokinesia, tremor, and muscular rigidity. It results in a slowing of voluntary movements, a festinating gait, peculiar posture, and general weakness of muscles. There is progressive degeneration within the nuclear masses of the extrapyramidal system, and a characteristic loss of melanin-containing cells from the substantia nigra and a corresponding reduction in dopamine levels in the corpus striatum. The cause of PD is unknown, but it is widely believed that multifactorial genetic and environmental factors are contributors. While the disease can develop at any age, it is most common in adults, and typically afflicts people at about sixty years of age and older. Parkinson's disease is becoming a particularly serious disease given the aging population.

There are no known cures for PD. The most common treatment has been the administration of levodopa, the precursor to dopamine, whose concentration in the substantia nigra is known to diminish as the disease progresses. Levodopa often produces unpleasant complications, resulting in even more serious health problems that are untreatable.

There are a group of monomeric proteins called muscarinic receptors found throughout the body of animals, including humans. These muscarinic receptors are present in the central nervous system, the peripheral nervous system, and in peripheral organs. There have been five muscarinic receptor subtypes identified, and they are referred to as $M_1$, $M_2$, $M_3$, $M_4$, and $M_5$ receptors. The various receptors are present throughout the body, and the individual subtypes seem to be responsible for different actions. For example, in peripheral tissues, $M_1$ receptors amplify ganglionic neurotransmission. $M_2$ receptors are involved in contractility and heart rate, while $M_3$ receptors mediate contraction of smooth muscles. For muscarinic receptors in brain tissue, the $M_1$ receptors play a role in memory and learning, the $M_2$ receptors influence autonomic functions, and there is evidence that $M_4$ receptors control motor behavior.

Compounds that antagonize muscarinic receptors have been developed for treatment of neurodegenerative diseases such as PD. Because the various muscarinic receptor subtypes are expressed in numerous body tissues, and each subtype appears to control or effect a different bodily function, it would be useful to find compounds that are selective for a single subtype. The $M_4$ subtype is found in high levels in the striatum of the brain and is involved in motor function. Accordingly, compounds that selectively antagonize the $M_4$ receptor would be useful as treatments for PD, without adversely affecting other body functions controlled by the other muscarinic receptor subtypes.

SUMMARY OF THE INVENTION

The present invention provides compounds that are useful in a method of selectively antagonizing the $M_4$ muscarinic receptor, the method comprising the administration of an effective amount of such a compound to a subject, preferably mammalian, in need thereof.

The present invention is directed to fused-ring derivatives containing an indole and their use as antagonists of the $M_4$ muscarinic receptor. The compounds of the invention are those having the structure of Formula I:

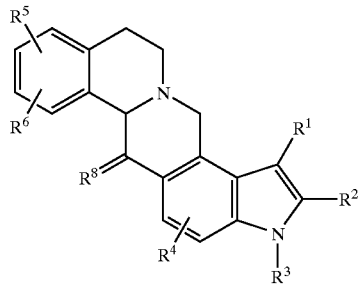

wherein:
  $R^1$ is hydrogen, lower alkyl or $COOR^7$, or aryl, heteroaryl, arylalkyl or heteroarylalkyl optionally substituted with one, two, or three groups independently selected from hydrogen, halogen, lower alkyl, lower alkoxy, hydroxy, cyano, nitro, amino, mono- or dialkylamino, carboxy, alkoxycarbonyl, carbamoyl, sulfamoyl, trifluoromethyl, or alkylthio;
  $R^3$ is hydrogen or lower alkyl;
  $R^2$, $R^4$, $R^5$, and $R^6$ independently represent hydrogen, halogen, lower alkyl, lower alkoxy, hydroxy, cyano, nitro, amino, mono- or dialkylamino, carboxy, alkoxycarbonyl, carbamoyl, sulfamoyl, trifluoromethyl, or alkylthio;
  $R^7$ is hydrogen or lower alkyl;
  —may or may not be a bond; and
  $R^8$ is hydrogen or oxo.

The instant invention includes pharmaceutical compositions of compounds of Formula 1 and a method of treating PD, the method comprising administering to a patient having PD a therapeutically effective amount of a compound of Formula I.

Also provided is a method of selectively antagonizing the $M_4$ muscarinic receptor, the method comprising administering to a patient in need selectively antagonizing the $M_4$ muscarinic receptor an $M_4$ muscarinic receptor antagonizing amount of a compound of Formula I.

DETAILED DESCRIPTION OF THE INVENTION

The novel compounds encompassed by the instant invention are those described by the general Formula I set forth above, and the pharmaceutically acceptable salts, esters, amides, and prodrugs thereof Preferred compounds of Formula I are those in which $R^1$ is $COOR^7$; $R^2$ is lower alkyl or (un)substituted aryl or heteroaryl; $R^3$ is hydrogen; $R^4$ is hydrogen or halogen; $R^5$ is lower alkoxy, alkylthio, lower alkyl, or halogen; $R^6$ is hydrogen; $R^7$ is lower alkyl; and $R^8$ is hydrogen.

More preferred compounds of Formula I are those where $R^2$ are methyl, ethyl, n-propyl, or (un)substituted heteroaryl; $R^4$ is hydrogen or bromo; and $R^5$ is lower alkyl or alkylthio.

In addition to the compounds of Formula I, the invention encompasses compounds of Formula II:

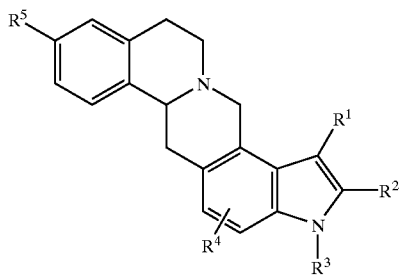

II wherein $R^1$, $R^2$, $R^3$, $R^4$, and $R^5$ are as defined above for Formula I.

Preferred compounds of Formula II are those where $R^1$ is $COOR^7$; $R^2$ is lower alkyl or (un)substituted aryl or heteroaryl; $R^3$ is hydrogen; $R^4$ is hydrogen or halogen; $R^5$ is lower alkoxy, alkylthio, lower alkyl, or halogen; and $R^7$ is lower alkyl.

In addition, the invention encompasses compounds of Formula III:

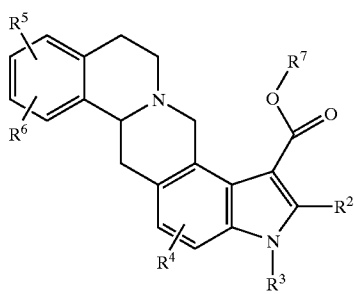

III wherein $R^2$, $R^3$, $R^4$, $R^5$, and $R^6$ are as defined above for Formula I.

Preferred compounds of Formula III are those where $R^2$ is lower alkyl or (un)substituted aryl or heteroaryl; $R^3$ is hydrogen; $R^4$ is hydrogen or halogen; $R^5$ is lower alkoxy, alkylthio, lower alkyl, or halogen; $R^6$ is hydrogen; and $R^7$ is lower alkyl.

In addition, the invention encompasses compounds of Formula IV:

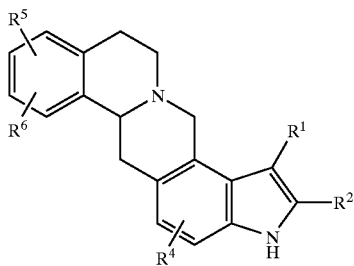

IV

Preferred compounds of Formula IV are those in which $R^1$ is $COOR^7$; $R^2$ is lower alkyl or (un)substituted aryl or heteroaryl; $R^4$ is hydrogen or halogen; $R^5$ is lower alkoxy, alkylthio, lower alkyl, or halogen; $R^6$ is hydrogen; and $R^7$ is lower alkyl.

Except as expressly defined otherwise, the following definition of terms is employed throughout this specification.

The terms "alkyl," "lower alkyl," or "$(C_1-C_6)$-alkyl" mean a straight or branched hydrocarbon having from 1 to 6 carbon atoms and includes, for example, methyl, ethyl, n-propyl, isopropyl, n-butyl, sec-butyl, isobutyl, tert-butyl, n-pentyl, n-hexyl, and the like. The alkyl group can also be substituted with one or more of the substituents listed below for aryl.

By "alkoxy," "lower alkoxy," or "$(C_1-C_6)$-alkoxy" in the present invention is meant straight or branched chain alkoxy groups having 1 to 6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

The term "halogen" includes chlorine, fluorine, bromine, and iodine, and their monovalent radicals.

The term "aryl" means an aromatic carbocyclic group having a single ring (e.g., phenyl), multiple rings (e.g., biphenyl), or multiple condensed rings in which at least one is aromatic (e.g., 1,2,3,4-tetrahydronaphthyl, naphthyl, anthryl, or phenanthryl), unsubstituted or substituted by 1 to 3 substituents selected from alkyl, O-alkyl and S-alkyl, OH, SH, —CN, halogen, 1,3-dioxolanyl, $CF_3$, $NO_2$, $NH_2$, $NHCH_3$, $N(CH_3)_2$, NHCO-alkyl, —$(CH_2)_mCO_2H$, —$(CH_2)_m$ $CO_2$-alkyl, —$(CH_2)_mSO_3H$, —NH alkyl, —N(alkyl)$_2$, —$(CH_2)_mPO_3H_2$, —$(CH_2)_mPO_3(alkyl)_2$, —$(CH_2)_mSO_2NH_2$, and —$(CH_2)_mSO_2NH$-alkyl wherein alkyl is defined as above and m is 0, 1, 2, or 3. A preferable aryl group of the present invention is phenyl.

The term "aralkyl" or "arylalkyl" means an alkyl moiety (as defined above) substituted with an aryl moiety (also as defined above).

By heteroaryl (aromatic heterocycle) in the present invention is meant one or more aromatic ring systems of 5-, 6-, or 7-membered rings containing at least one, and up to four heteroatoms selected from nitrogen, oxygen, or sulfur. Such heteroaryl groups include, for example, thienyl, furanyl, thiazolyl, imidazolyl, (is)oxazolyl, pyridyl, pyrimidinyl, (iso)quinolinyl, naphthyridinyl, benzimidazolyl, and benzoxazolyl. The heterocycle is unsubstituted or substituted by 1 to 3 substituents selected from alkyl, O-alkyl and S-alkyl, OH, SH, —CN, halogen, 1,3-dioxolanyl, $CF_3$, $NO_2$, $NH_2$, $NHCH_3$, $N(CH_3)_2$, NHCO-alkyl, —$(CH_2)_mCO_2H$, —$(CH_2)_m$ $CO_2$-alkyl, —$(CH_2)_mSO_3H$, —NH alkyl, —N(alkyl)$_2$, —$(CH_2)_mPO_3H_2$, —$(CH_2)_mPO_3(alkyl)_2$, —$(CH_2)_mSO_2NH_2$, and —$(CH_2)_mSO_2NH$ —alkyl wherein alkyl is defined as above and m is 0, 1, 2, or 3. A preferable -heteroaryl group of the present invention is 2-, 3-, or 4-pyridine.

The term "heteroarylalkyl" means an alkyl moiety (as defined above) substituted with an heteroaryl moiety (also as defined above).

The symbol "—" means a covalent bond. "$M_4$ selective binding" means that a compound binds to the $M_4$ muscarinic receptor subtype by at least about 20-fold more than to any of the other receptor subtypes ($M_1$, $M_2$, $M_3$, and $M_5$).

The term "pharmaceutically acceptable salt, ester, amide, and prodrug" as used herein refers to the amino acid addition salts of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively nontoxic, inorganic, and organic acid addition salts of compounds of the present invention. These salts can be prepared in situ during the final isolation and purification of the compounds, or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactiobionate and laurylsulphonate salts, and the like. These may include cations based on the alkali and alkaline earth metals, such as sodium, lithium, potassium, calcium, magnesium, and the like, as well as, nontoxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, Berge S. M., et al., Pharmaceutical Salts, *J. Pharm. Sci.*, 1977;66:1–19, which is incorporated herein by reference.)

Examples of pharmaceutically acceptable, nontoxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines, the amine may also be in the form of a 5- or 6-membered heterocycle containing one nitrogen atom. Amides derived from ammonia, $C_1$–$C_3$ alkyl primary amides and $C_1$–$C_2$ dialkyl secondary amides are preferred. Amides of the compounds of the invention may be prepared according to conventional methods.

The term "prodrug" refers to compounds that are rapidly transformed in vivo to yield the parent compound of the above formulas, for example, by hydrolysis in blood. A thorough discussion is provided in T. Higuchi and V. Stella, *Pro-drugs as Novel Delivery Systems,* Vol. 14 of the A.C.S. Symposium Series, and in *Bioreversible Carriers in Drug Design* ed. Edward B. Roche, American Pharmaceutical Association and Pergamon Press, 1987, both of which are incorporated herein by reference.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

Certain of the compounds of the present invention possess one or more chiral centers and each center may exist in the R or S configuration. The present invention includes all diastereomeric, enantiomeric, and epimeric forms as well as the appropriate mixtures thereof. Additionally, the compounds of the present invention may exist as geometric isomers. The present invention includes all cis, trans, syn, anti, entgegen (E), and zusammen (Z) isomers as well as the appropriate mixtures thereof.

Representative compounds of the invention are shown below in Table 1.

TABLE 1

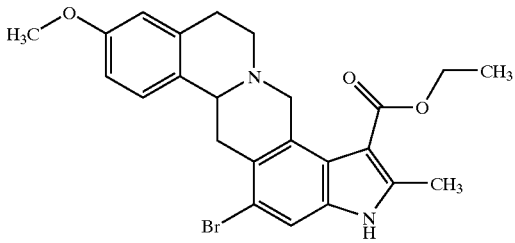

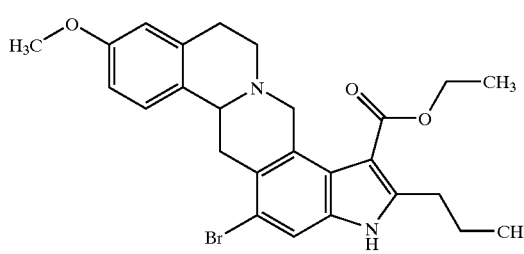

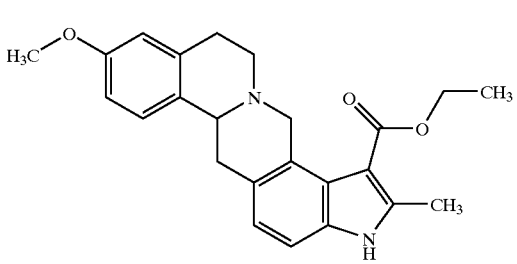

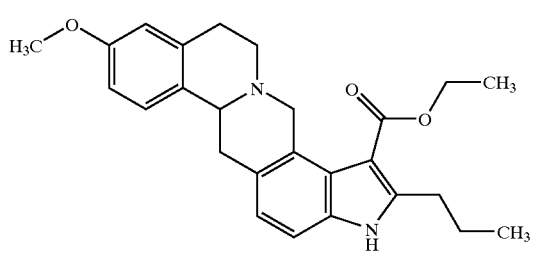

Representative compounds of the present invention, which are encompassed by Formula I include, but are not limited to the compounds in Table 1 and their pharmaceutically acceptable acid or base addition salts, or amide, or prodrugs thereof.

In the methods of the present invention, a compound can be administered either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft- and hard-filled gelatin capsules using such excipients as lactose or milk sugar, as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, and sesame oil, glycerol, tetrahydrofurfuryl alcohol, polyethyleneglycols, and fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administrations are preferably suppositories which can be prepared by mixing the compounds of the present invention with suitable nonirritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers or propellants as may be required. Ophthalmic formulations, eye ointments, powders, and solutions are also contemplated as being within the scope of this invention.

The compounds of the present invention can be administered to a patient at dosage levels in the range of about 0.1 to about 1000 mg/day, and generally from about 5 to about 250 mg/kg/day. For a normal human adult having a body weight of about 70 kg, a dosage in the range of about 0.01 to about 100 mg/kg of body weight per day is sufficient. The specific dosage used, however, can vary. For example, the dosage can depend on a number of factors including the requirements of the patient, the severity of the condition being treated, and the pharmacological activity of the compound being used. The determination of optimum dosages for a particular patient is well-known to those skilled in the art. The term "patient" means humans and other animals.

For use in treating PD, the invention compound is typically part of a pharmaceutical composition and is administered to a patient by methods well-known to those skilled in the art. The invention compound will be present in an amount of about 5% to about 95% by weight of the composition.

The examples presented below are intended to illustrate particular embodiments of the invention, and are not intended to limit the scope of the specification or the claims in any way.

The compounds of Formula I are readily prepared by methods utilizing standard organic chemical reactions. An illustration of the preparation of compounds of the present invention is shown in Scheme 1. $R^2$, $R^5$, and $R^6$ are as defined above for Formula I.

Armed with the disclosure provided herein (particularly the schemes and the synthetic examples that follow) and knowledge common to all who practice in the field, those of ordinary skill in the art will be able to make and use the entire scope of compounds disclosed herein.

Scheme 1

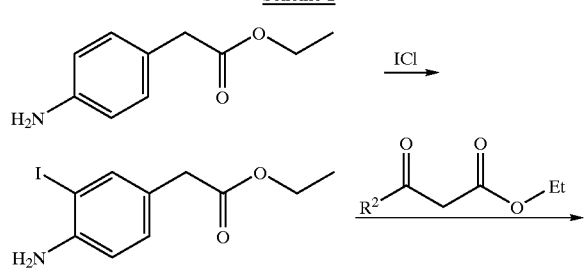

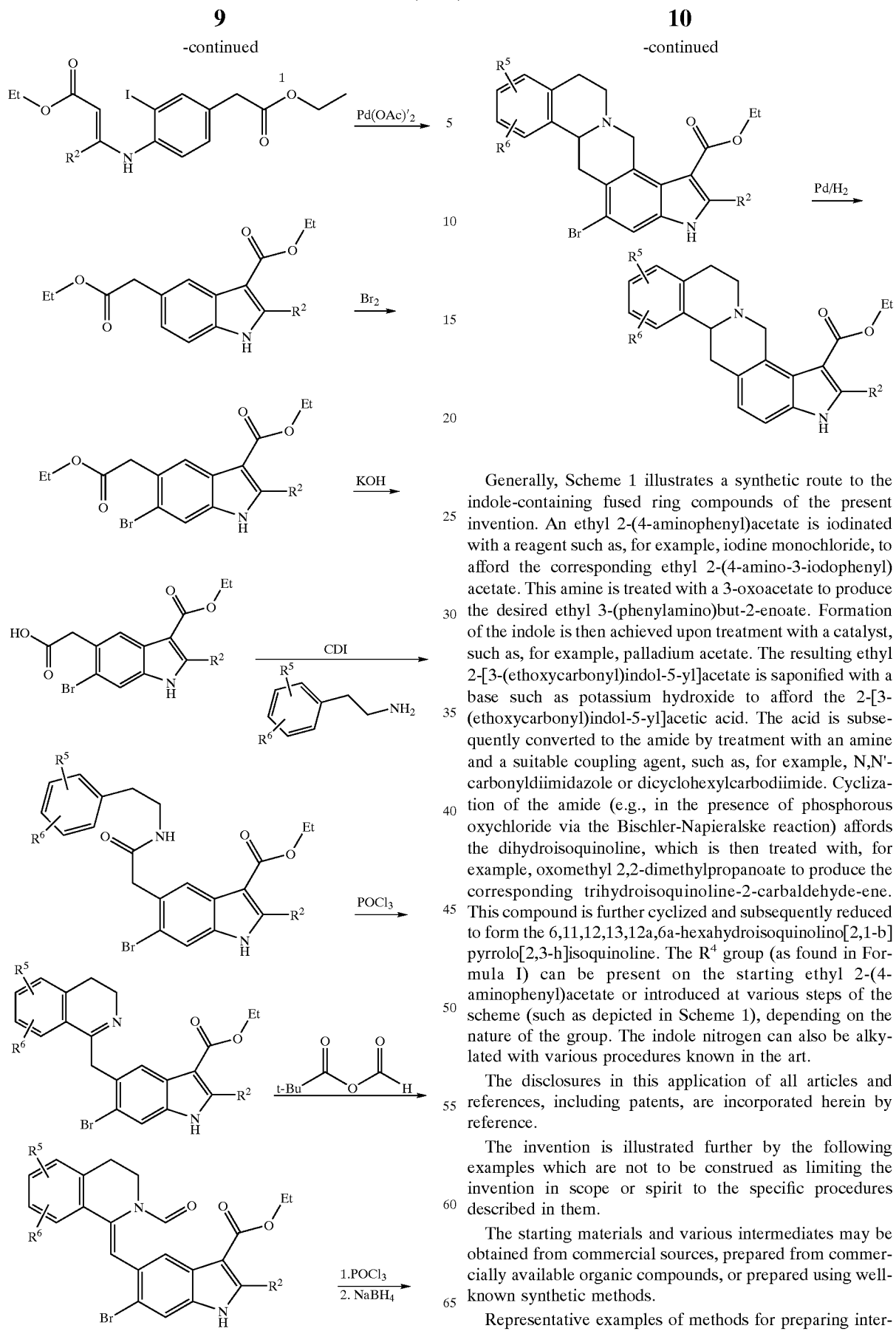

Generally, Scheme 1 illustrates a synthetic route to the indole-containing fused ring compounds of the present invention. An ethyl 2-(4-aminophenyl)acetate is iodinated with a reagent such as, for example, iodine monochloride, to afford the corresponding ethyl 2-(4-amino-3-iodophenyl) acetate. This amine is treated with a 3-oxoacetate to produce the desired ethyl 3-(phenylamino)but-2-enoate. Formation of the indole is then achieved upon treatment with a catalyst, such as, for example, palladium acetate. The resulting ethyl 2-[3-(ethoxycarbonyl)indol-5-yl]acetate is saponified with a base such as potassium hydroxide to afford the 2-[3-(ethoxycarbonyl)indol-5-yl]acetic acid. The acid is subsequently converted to the amide by treatment with an amine and a suitable coupling agent, such as, for example, N,N'-carbonyldiimidazole or dicyclohexylcarbodiimide. Cyclization of the amide (e.g., in the presence of phosphorous oxychloride via the Bischler-Napieralske reaction) affords the dihydroisoquinoline, which is then treated with, for example, oxomethyl 2,2-dimethylpropanoate to produce the corresponding trihydroisoquinoline-2-carbaldehyde-ene. This compound is further cyclized and subsequently reduced to form the 6,11,12,13,12a,6a-hexahydroisoquinolino[2,1-b]pyrrolo[2,3-h]isoquinoline. The $R^4$ group (as found in Formula I) can be present on the starting ethyl 2-(4-aminophenyl)acetate or introduced at various steps of the scheme (such as depicted in Scheme 1), depending on the nature of the group. The indole nitrogen can also be alkylated with various procedures known in the art.

The disclosures in this application of all articles and references, including patents, are incorporated herein by reference.

The invention is illustrated further by the following examples which are not to be construed as limiting the invention in scope or spirit to the specific procedures described in them.

The starting materials and various intermediates may be obtained from commercial sources, prepared from commercially available organic compounds, or prepared using well-known synthetic methods.

Representative examples of methods for preparing intermediates of the invention are set forth below.

EXAMPLE 1

Synthesis of 5-bromo-9-methoy-2-methyl-6,11,12,
13-tetrahydro-3H,6aH-3,12a-diaza-benzo[a]
cyclopent[h]anthracene-1-carboxylic acid ethyl ester
(Compound 1)

1. (4-Amino-3-iodo-phenyl)acetic acid ethyl ester

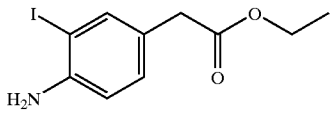

To a cooled solution (5° C.) of (4-aminophenyl)acetic acid ethyl ester (25 g, 0.39 mol) in $CH_2Cl_2$ (150 mL) is added triethylamine (14.1 g, 0.139 mmol) followed by a solution of iodine monochloride (21.5 g, 0.132 mol) in $CH_2Cl_2$ (100 mL). Cooling is removed and the reaction mixture is stirred for 4 hours at room temperature. The solution is concentrated in vacuo and chromatographed with a gradient of hexane/ethyl acetate (5%–30%) within 1 hour to give the desired product (19.5 g, 46%). MS: 305.9 (M+1)$^+$.

2. 3-(4-Ethoxycarbonylmethyl-2-iodo-phenylamino)but-2-enoic acid ethyl ester

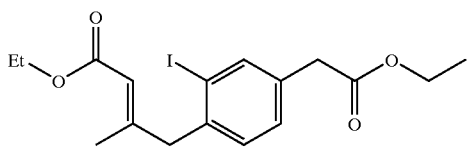

A solution of (4-amino-3-iodo-phenyl)acetic acid ethyl ester (9.85 g, 32.3 mmol), ethyl acetoacetate (4.2 g, 32.3 mmol), and toluenesulfonic acid monohydrate (0.3 g, 1.6 mmol) in benzene (150 mL) is refluxed under Dean-Stark conditions overnight. The solution is then cooled to room temperature and washed with sodium bicarbonate ($NaHCO_3$) (2×50 mL) and concentrated in vacuo to give the desired product (12.5 g, 93%). The product is used without further purification in Step 3. MS: 418 (M+1)$^+$.

3. 5-Ethoxycarbonylmethyl-2-methyl-1H-indole-3-carboxylic acid ethyl ester

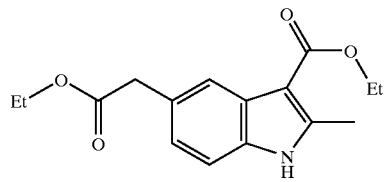

To a solution of 3-(4-ethoxycarbonylmethyl-2-iodo-phenylamino)but-2-enoic acid ethyl ester (12.5 g, 30 mmol) in DMF (30 mL), tripropylamine (4.3 g, 30 mmol), and Pd(II)acetate (0.33 g, 1.5 mmol) are added, and the reaction mixture is heated at 120° C. for 1 hour. After cooling to room temperature, ethyl acetate (150 mL) is added. The organic layer is washed with water (2×100 mL), dried ($Na_2SO_4$), filtered, and concentrated in vacuo. The crude material is recrystallized from hexane/ethyl acetate to give a yellow-orange solid (3.3 g, 38%). MS: 290 (M+1)$^+$.

4. 6-Bromo-5-ethoxycarbonylmethyl-2-methyl-1H-indole-3-carboxylic acid ethyl ester

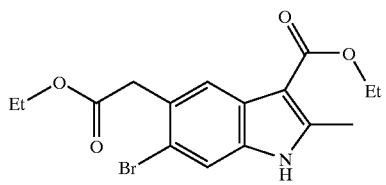

To a solution of 5-ethoxycarbonylmethyl-2-methyl-1H-indole-3-carboxylic acid ethyl ester (3 g, 10.4 mmol) in acetic acid (20 mL) is added bromine (1.65 g, 10.4 mmol) dropwise, and the reaction mixture is stirred for 10 minutes. The solution is then concentrated in vacuo and chromatographed with a gradient of hexane/ethyl acetate (5%–30%) within 30 minutes to afford a yellow solid (3.3 g, 86%). MS: 368, 370 (M+1)$^+$.

5. 6-Bromo-5-carboxymethyl-2-methyl-1H-indole-3-carboxylic acid ethyl ester

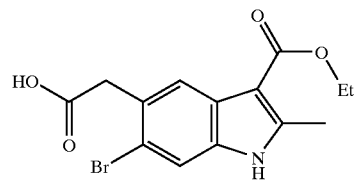

To a solution of 6-bromo-5-ethoxycarbonylmethyl-2-methyl-1H-indole-3-carboxylic acid ethyl ester (3 g, 8.1 mmol) in ethanol (30 mL) is added 4.6N KOH (3 mL; 9.8 mmol), and the reaction mixture is stirred at 45° C. for 4 hours and then at room temperature overnight. The solution is concentrated in vacuo and then ethyl acetate (150 mL) and water (150 mL) are added. The organic layer is extracted with water (50 mL), the combined water layers are then acidified with HCl (20%) to pH<2. The aqueous layers are then extracted with ethyl acetate (2×100 mL), dried ($Na_2SO_4$), filtered, and concentrated to give the desired product (1.85 g, 66%). MS: 340, 342 (M+1)$^+$.

6. 6-Bromo-5-[2-(3-methyl-phenyl)-ethylcarbamoylmethyl]-2-methyl-1H-indole-3-carboxylic acid ethyl ester

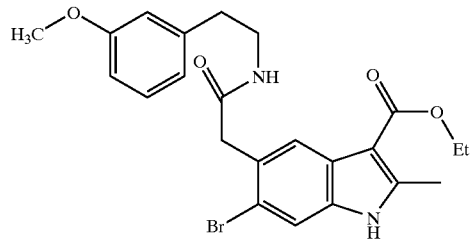

To a solution of CDI (0.93 g, 5.7 mmol) in THF (50 mL) is added a solution of 6-bromo-5-carboxymethyl-2-methyl-1H-indole-3-carboxylic acid ethyl ester in THF (50 mL). The mixture is stirred at room temperature for 45 minutes, then refluxed for 1 hour. After cooling the reaction mixture to room temperature, 2-(3-methoxyphenyl)ethylamine is added and resulting reaction mixture is stirred at room temperature overnight. The reaction mixture is concentrated in vacuo, ethyl acetate (150 mL) is added, then washed with 1N HCl (50 mL), 1N NaOH (50 mL), and brine (50 mL). The organic layer is dried ($Na_2SO_4$) and concentrated in vacuo to give the desired product (2.15 g, 84%). MS: 473, 475 (M+1)$^+$.

7. 6-Bromo-5-(6-methoxy-3,4-dihydro-isoquinoline-1-ylmethyl)-2-methyl-1H-indole-3-carboxylic acid ethyl ester

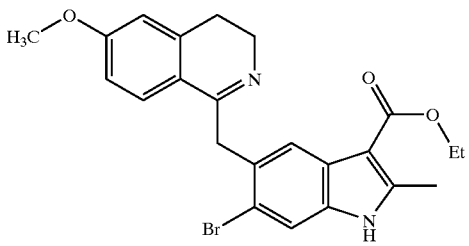

To a solution of 6-bromo-5-[2-(3-methyl-phenyl)-ethylcarbamoylmethyl]-2-methyl-1H-indole-3-carboxylic acid ethyl ester (2.15 g, 4.5 mmol) in benzene (20 mL) is added dropwise $POCl_3$ (10 mL; 107 mmol), and the mixture is refluxed for 1 hour. After the reaction mixture is cooled to room temperature, hexane (3×100 mL) is added, stirred for 5 minutes, and decanted. The dark residue is then dissolved in $CH_2Cl_2$ (150 mL), washed with $NaHCO_3$ (2×50 mL), brine (2×100 mL), and dried with $Na_2SO_4$. The solution is filtered and concentrated in vacuo to afford the desired product (2.03 g, 99%). MS: 455, 457 (M+1)$^+$.

8. 6-Bromo-5(2-formyl-6-methoxy-3,4-dihydro-2H-isoquinoline-1-ylidenemethyl)2-methyl-1H-indole-3-carboxylic acid ethyl ester

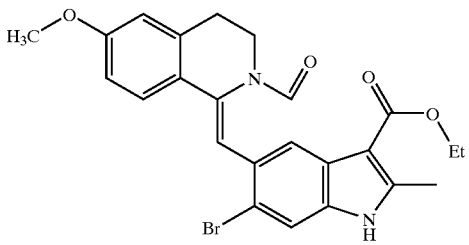

To a solution of 6-bromo-5-(6-methoxy-3,4-dihydro-isoquinoline-1-ylmethyl)-2-methyl-1H-indole-3-carboxylic acid ethyl ester (2.03 g, 4.5 mmol) in $CH_2Cl_2$ (50 mL) is added pyridine (2.3 g, 30 mmol) and 3N formic pivalic anhydride (5 mL; 14.5 mmol) at 0° C., and the reaction is stirred at room temperature for 3 hours. $CH_2Cl_2$ (50 mL) is then added to the reaction mixture and the organic layer is washed with water (2×50 mL), IN HCl (50 mL), 1N NaOH (50 mL), and brine (50 mL). The solution is dried ($Na_2SO_4$), filtered, and concentrated in vacuo to give the desired product (1.3 g, 60%). MS: 483, 485 (M+1)$^+$.

9. 5-Bromo-9-methoxy-2-methyl-6,11,12,13-tetrahydro-3H,6aH-3,12a-diaza-benzo[a]cyclopent[h]anthracene-1-carboxylic acid ethyl ester To a solution of 6-bromo-5-(2-formyl-6-methoxy-3,4-dihydro-2H-isoquinoline-1-ylidenemethyl)-2-methyl-1H-indole-3-carboxylic acid ethyl ester (1.3 g, 2.7 mmol) in benzene is added $POCl_3$ (10 mL; 107 mmol), and the reaction mixture is refluxed for 1 hour. Hexane (3×100 mL) is added, the mixture is stirred for 5 minutes, and then decanted. The dark residue is dissolved in methanol and $NaBH_4$ (1.8 g, 50 mmol) is added portion-wise at 0° C. After the addition is completed, the suspension is refluxed for 1 hour and concentrated in vacuo. The residue is dissolved in $CH_2Cl_2$ (100 mL) and water (100 mL). The organic layer is separated, washed with brine (100 mL) and $NaHCO_3$ (50 mL), dried with $Na_2SO_4$, and concentrated to yield a crude oil (1.3 g). Ethanol (3 mL) is added and white crystals precipitate. The solid material is filtered and recrystallized from ethanol to afford the desired product (Compound 1) (0.23 g, 18%). MS: 469, 471 (M+1)$^+$.

Analysis for $C_{24}H_{25}BrN_2O_3 \times 1.24\ H_2O$: Calcd: C, 58.61; H, 5.65; N, 5.68. Found: C, 58.99; H, 5.69; N, 5.28.

EXAMPLE 2

Synthesis of 9-methoxy-2-methyl-6,11,12,13-tetrahydro-3H,6aH-3,12a-diaza-benzo[a]cyclopent[h]anthracene-1-carboxylic acid ethyl ester (Compound 3)

To a solution of 5-bromo-9-methoxy-2-methyl-6,11,12,13-tetrahydro-3H,6aH-3,12a-diaza-benzo[a]cyclopent[h]anthracene-1-carboxylic acid ethyl ester (Example 1, Step 9) (0.2 g, 0.42 mmol) in THF/ethanol 1:1 (30 mL) is added palladium on carbon (20%). The suspension is hydrogenated for 8 hours. The catalyst is filtered and the solution is concentrated in vacuo. Ethanol (1 mL) is added and white crystals precipitated. The solid material is filtered and recrystallized from ethanol to afford the desired product (Compound 3) (0.09 g, 54%). MS: 391.1 (M+1)$^+$.

Exact mass: 391.2014 (M+1)$^+$; $C_{24}H_{26}N_2O_3$.

EXAMPLE 3

The following compounds are prepared essentially according to the procedures described in Examples 1 and 2 and shown in Scheme 1:

(a) 5-Bromo-9-methoxy-2-propyl-6,11,12,13-tetrahydro-3H6aH-3,12a-diaza-benzo[a]cyclopent[h]anthracene-1-carboxylic acid ethyl ester (Compound 2). MS: 497, 499 (M+1)$^+$.

Exact mass: 497.1435 (M+1)$^+$; $C_{26}H_{29}BrN_2O_3$;

(b) 9-Methoxy-2-propyl-6,11,12,13-tetrahydro-3H6aH-3,12a-diaza-benzo[a]cyclopent[h]anthracene-1-carboxylic acid ethyl ester (Compound 4). MS: 419.2 (M+1)$^+$.

Exact mass: 419.2332 (M+1)$^+$; $C_{26}H_{30}N_2O_3$.

EXAMPLE 4

The compounds of Formula I have shown potent binding affinity for muscarinic receptors and are thus useful as muscarinicing antagonists. The compounds are surprisingly selective as muscarinic $M_4$ receptor antagonists. The compounds are evaluated in standard assays used to measure muscarinic receptor binding. Specifically, the compounds are evaluated for their binding affinity toward five human muscarinic receptor subtypes ($M_1$–$M_5$) by the method of Dorje et al., *J. Pharm. Exp. Ther.*, 1991;256:727–733, incorporated herein by reference. The binding is determined by measuring the displacement of [$^3$H]-NMS binding using membranes from transfected Chinese hamster ovary (CHO) cells. All compounds are tested two to four times with duplicate tubes (SEM is ≦10% in all cases). Table 2 shows the binding activities ($IC_{50}$ nM) of various compounds of the invention.

TABLE 2

| [$^3$H]-NMS Receptor Binding in CHO Cell Membranes $IC_{50}$ (μm) | | | | | |
|---|---|---|---|---|---|
| Compound | Hm1 | Hm2 | Hm3 | Hm4 | Hm5 |
| 1 | 0.4 | 3 | >10, 20 | 3.0, 0.6 | 5, 4 |
| 2 | 0.5, 0.4 | 0.8, 4 | >10, 50 | 2, 3 | 10, 15 |

TABLE 2-continued

| | [³H]-NMS Receptor Binding in CHO Cell Membranes IC$_{50}$ ($\mu$m) | | | | |
|---|---|---|---|---|---|
| Compound | Hm1 | Hm2 | Hm3 | Hm4 | Hm5 |
| 3 | >10, 25 | 50, 25 | >10, 5 | >10, 20 | 10, 9 |
| 4 | >10, 50 | 20, 15 | >10, 10 | >10, 50 | 50, 50 |

The invention and the manner and process of making and using it are now described in such full, clear, concise, and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the Formula I or a pharmaceutically acceptable salt, ester, amide, or prodrug thereof, wherein $R^1$ is hydrogen, lower alkyl, or COOR$^7$, or aryl, heteroaryl, arylalkyl, or heteroarylalkyl optionally substituted with one, two, or three groups independently selected from hydrogen, halogen, lower alkyl, lower alkoxy, hydroxy, cyano, nitro, amino, mono- or dialkylamino, carboxy, alkoxycarbonyl, carbamoyl, sulfamoyl, trifluoromethyl, or alkylthio;

$R^3$ is hydrogen or lower alkyl;

$R^2$, $R^4$, $R^5$, and $R^6$ independently represent hydrogen, halogen, lower alkyl, lower alkoxy, hydroxy, cyano, nitro, amino, mono- or dialkylamino, carboxy, alkoxycarbonyl, carbamoyl, sulfamoyl, trifluoromethyl, or alkylthio; and $R^7$ is hydrogen or lower alkyl;

—may or may not be a bond; and $R^8$ is hydrogen or oxo.

2. A compound of the Formula II or a pharmaceutically acceptable salt, ester, amide, or prodrug thereof, wherein $R^1$ is hydrogen, lower alkyl, or COOR$^7$, or aryl, heteroaryl, arylalkyl, or heteroarylalkyl optionally substituted with one, two, or three groups independently selected from hydrogen, halogen, lower alkyl, lower alkoxy, hydroxy, cyano, nitro, amino, mono- or dialkylamino, carboxy, alkoxycarbonyl, carbamoyl, sulfamoyl, trifluoromethyl, or alkylthio;

$R^3$ is hydrogen or lower alkyl;

$R^2$, $R^4$, and $R^5$ independently represent hydrogen, halogen, lower alkyl, lower alkoxy, hydroxy, cyano, nitro, amino, mono- or carboxy, alkoxycarbonyl, carbamoyl, sulfamoyl, trifluoromethyl, or alkylthio; and $R^7$ is hydrogen or lower alkyl.

3. A compound of the Formula III or a pharmaceutically acceptable salt, ester, amide, or prodrug thereof, wherein $R^3$ is hydrogen or lower alkyl;

$R^2$, $R^4$, $R^5$, and $R^6$ independently represent hydrogen, halogen, lower alkyl, lower alkoxy, hydroxy, cyano, nitro, amino, mono- or dialkylamino, carboxy, alkoxycarbonyl, carbamoyl, sulfamoyl, trifluoromethyl, or alkylthio; and $R^7$ is hydrogen or lower alkyl.

4. A compound of the Formula IV

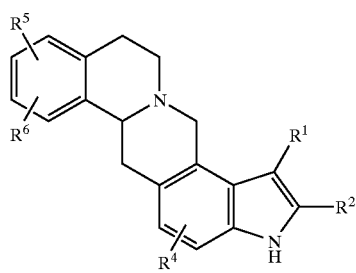

or a pharmaceutically acceptable salt, ester, amide, or prodrug thereof,
wherein
$R^1$ is hydrogen, lower alkyl, or $COOR^7$, or
aryl, heteroaryl, arylalkyl, or heteroarylalkyl optionally substituted with one, two, or three groups independently selected from hydrogen, halogen, lower alkyl, lower alkoxy, hydroxy, cyano, nitro, amino, mono- or dialkylamino, carboxy, alkoxycarbonyl, carbamoyl, sulfamoyl, trifluoromethyl, or alkylthio;
$R^2$, $R^4$, $R^5$, and $R^6$ independently represent hydrogen, halogen, lower alkyl lower alkoxy, hydroxy, cyano, nitro, amino, mono- or dialkylamino, carboxy, alkoxycarbonyl, carbamoyl, sulfamoyl, trifluoromethyl, or alkylthio; and
$R^7$ is hydrogen or lower alkyl.

5. A compound according to claim 1 wherein $R^1$ is $COOR^7$.

6. A compound according to claim 5 wherein $R^7$ is lower alkyl.

7. A compound according to claim 1 wherein $R^2$ is lower alkyl.

8. A compound according to claim 7 wherein $R^2$ is selected from methyl or n-propyl.

9. A compound according to claim 1 wherein $R^3$ is hydrogen.

10. A compound according to claim 1 wherein $R^4$ is selected from hydrogen or halogen.

11. A compound according to claim 1 wherein $R^6$ is hydrogen.

12. A compound according to claim 1 wherein $R^5$ is lower alkoxy.

13. A compound according to claim 1 which is selected from:
Ethyl 5-bromo-9-methoxy-2-methyl-6,11,12,13,12a,6a-hexahydroisoquinolino[2,1-b]pyrrolo[2,3-h]isoquinolinecarboxylate;
Ethyl 5-bromo-9-methoxy-2-propyl-6,11,12,13,12a,6a-hexahydroisoquinolino[2,1-b]pyrrolo[2,3-h]isoquinolinecarboxylate;
Ethyl 9-methoxy-2-methyl-6,11,12,13,12a,6a-hexahydroisoquinolino[2,1-b]pyrrolo[2,3-h]isoquinolinecarboxylate; and
Ethyl 9-methoxy-2-propyl-6,11,12,13,12a,6a-hexahydroisoquinolino[2,1-b]pyrrolo[2,3-h]isoquinolinecarboxylate.

14. A pharmaceutical composition comprising a compound of claim 1 together with a pharmaceutically acceptable diluent, excipient, or carrier therefore.

15. A method for treating Parkinson's disease comprising administering to a patient suffering from Parkinson's disease, and in need of treatment, an effective amount of a compound of Formula I.

* * * * *

UNITED STATES PATENT AND TRADEMARK OFFICE
CERTIFICATE OF CORRECTION

PATENT NO. : 6,500,837 B2
DATED : December 31, 2002
INVENTOR(S) : Augelli-Szafran et al.

It is certified that error appears in the above-identified patent and that said Letters Patent is hereby corrected as shown below:

<u>Column 16,</u>
Line 34, insert -- dialkylamino, -- after the word "or".

<u>Column 17,</u>
Line 26, insert -- , -- after the word "alkyl".

Signed and Sealed this

Twenty-ninth Day of July, 2003

JAMES E. ROGAN
*Director of the United States Patent and Trademark Office*